United States Patent [19]

Dixon

[11] Patent Number: 5,445,032

[45] Date of Patent: Aug. 29, 1995

[54] LOAD TESTING APPARATUS AND METHOD FOR A PERSONNEL PLATFORM

[76] Inventor: Joe K. Dixon, 2334 Red Barn La., Charlotte, N.C. 28210

[21] Appl. No.: 303,431

[22] Filed: Sep. 9, 1994

[51] Int. Cl.$^6$ ............................................. G01N 3/00
[52] U.S. Cl. .................................... 73/788; 73/865.9
[58] Field of Search ................. 73/788, 865.6, 865.9, 73/862.42

[56] References Cited

U.S. PATENT DOCUMENTS

| | | | |
|---|---|---|---|
| 4,702,320 | 10/1987 | Gano et al. | 166/343 |
| 4,884,454 | 12/1989 | Johnson | 73/788 |
| 5,096,018 | 3/1992 | Dickinson, Jr. | 182/63 |
| 5,332,274 | 7/1994 | Baumann | 294/63.3 |
| 5,356,250 | 10/1994 | Vogg et al. | 410/86 |

Primary Examiner—Richard E. Chilcot, Jr.
Assistant Examiner—Max H. Noori
Attorney, Agent, or Firm—Clifton Ted Hunt

[57] ABSTRACT

This invention relates to a personnel platform built to be occupied by workmen and suspended from a crane at an elevated work site, and to an apparatus and method for load testing a suspended personnel platform.

The load testing apparatus of this invention uses a personnel platform with forklift tubes and a plurality of latching assemblies integrated with a preformed test-weight. The latching assemblies include slidable lock-bolts that are easily and releasably engageable with the forklift tubes.

6 Claims, 5 Drawing Sheets

LOAD TESTING APPARATUS AND METHOD FOR A PERSONNEL PLATFORM

FIELD OF THE INVENTION

This invention relates to a personnel platform built to be occupied by workmen and suspended from a crane at an elevated work site, and to an apparatus and method for load testing a suspended personnel platform.

BACKGROUND OF THE INVENTION

Personnel platforms (sometimes known as "crane baskets" or "man-baskets") are conventionally used with a crane for vertical transportation of workers and equipment to a worksite above ground, an electric power line, for example.

The Occupational Safety and Health Administration (OSHA) is empowered (29 C.F.R. 1926.550) to require a trial lift and proof testing of a crane and its personnel platform at each set-up of the crane immediately before using the personnel platform with workmen in it.

The purpose of the trial lift and proof test (sometimes herein collectively called a load test) is to insure that the personnel platform can be safely used in each work position. Specifically, the load test (1) helps to determine whether the outrigger pads are on firm and even ground and whether the outrigger pads will sink down in the work position selected for use; (2) checks to be sure that the crane is within the 50% of rated lift capacity when in the selected work position; (3) checks to be sure that the load line is working properly and does not fail with the intended load; and (4) checks the four leg bridle to insure that it is capable of lifting the intended load.

TRIAL LIFT AND PROOF TEST

A trial lift is conducted by attaching a specified amount of weight to the personnel platform and positioning the personnel platform with the attached weight in one or more work positions intended to be used while the crane is at a particular location. The purpose of the trial lift is to determine whether the crane is within allowable working load limits and capable of handling the intended load.

A proof test is conducted by attaching a specified amount of weight to the personnel platform and using a crane to lift the unoccupied but weighted personnel platform off the ground and holding it above the ground for five minutes. The amount of weight varies with the rated capacities of the cranes and personnel platforms, but always amounts to hundreds of pounds and sometimes thousands of pounds.

The specified amount of weight can be provided with sandbags and other objects of known weight manually placed in the personnel platform, but that is such a time consuming and labor intensive method as to be economically infeasible. That fact has prompted efforts to simplify the attachment of the amount of weight specified by OSHA to a personnel platform in order to promote compliance with the OSHA requirements for load testing every time a crane or other lifting device is set up for operation with a personnel platform to lift personnel off the ground.

One attempt to simplify the attachment of the specified weight to a personnel platform is shown in U.S. Pat. No. 4,884,454, issued Dec. 5, 1989 to Johnson for MANBASKET TESTING APPARATUS AND METHOD. Johnson provides a single piece test-weight of a specified poundage to be used with the crane and personnel platform (termed a manbasket in the Johnson patent) to be tested. Johnson's test-weight is made with eyebolts extending upwardly from the upper surface of the test-weight. Johnson provides holes in the floor of his personnel platform (or manbasket) to receive the eyebolts when a crane is used to mount Johnson's manbasket on his test-weight. When the personnel platform is properly mounted for attachment to the test-weight, the eyebolts extend above the floor of the personnel platform.

Johnson then attaches his test-weight to the personnel platform by passing rods through the eyebolts that are above the floor of the personnel platform. The crane then lifts the personnel platform and the attached test weight to comply with the testing requirements of OSHA. At the completion of the test, the crane lowers the personnel platform and the attached test-weight to the ground. The rods are withdrawn from the eyebolts to remove the test-weight from the personnel platform. The crane then lifts the personnel platform without the test-weight to perform the assigned task with workmen in the personnel platform.

The Johnson apparatus and method is a big improvement over the manual loading of individual units of weight, such as sand bags, in a personnel platform. The Johnson apparatus does, however, have an objectionable disadvantage. The individual rods that Johnsons uses to attach the testweight to the personnel platform may be sometimes lost or misplaced. Other times they may be used for other purposes, such as prying up something, and become bent or misshapen.

In short, Johnson's rods are not reliable. They may be lost, bent or broken. Without the rods, the test-weight of Johnson's cannot be attached to the personnel platform and many hours of valuable time may be lost in getting replacement rods.

SUPERCAGE, a division of United States Crane, Inc., 1155 Central Florida Parkway, Orlando, Fla. 32859 markets a personnel platform and a test-weight for attachment to the personnel platform. The SUPERCAGE attachment apparatus comprises straps extending up from the sides of the test-weight and terminating adjacent flanges extending outwardly from the sides of the personnel platform, above its floor. The flanges have openings to receive bolts and bolts are used to attach the test-weight to the personnel platform.

The SUPERCAGE apparatus has the same disadvantage as the Johnson apparatus. The bolts are separate pieces and may be lost. Another disadvantage of the SUPERCAGE apparatus is that the test-weight is not attached to the floor of the personnel platform, with the result that the floor is not load tested.

SUMMARY OF THE INVENTION

The load testing apparatus of this invention uses a personnel platform with forklift tubes and a preformed test-weight of a specific weight with a plurality of latching assemblies formed integrally with the test-weight. The latching assemblies that are integral with the test-weight include slidable lock-bolts that are engageable with the forklift tubes to attach the test-weight to the personnel platform.

The preformed test-weight is illustrated in the preferred embodiment as a concrete filled pan, but the preformed test-weight may be a solid piece of steel, or otherwise, as desired.

More specifically, the load testing apparatus of the present invention comprises (1) a personnel platform with a floor and open ended forklift tubes beneath the floor; (2) a preformed test-weight having the amount of weight specified by OSHA for the crane and personnel platform to be tested; and (3) latching assemblies integrated with the test-weight and selectively engageable with the open ended forklift tubes to releasably attach the test-weight to a suspended personnel platform.

There are no loose parts, as in the prior art, and no risk of a critical piece, such as Johnson's rods or SUPERCAGES bolts, being missing when needed.

DETAILED DESCRIPTION OF THE INVENTION

Figure 1:
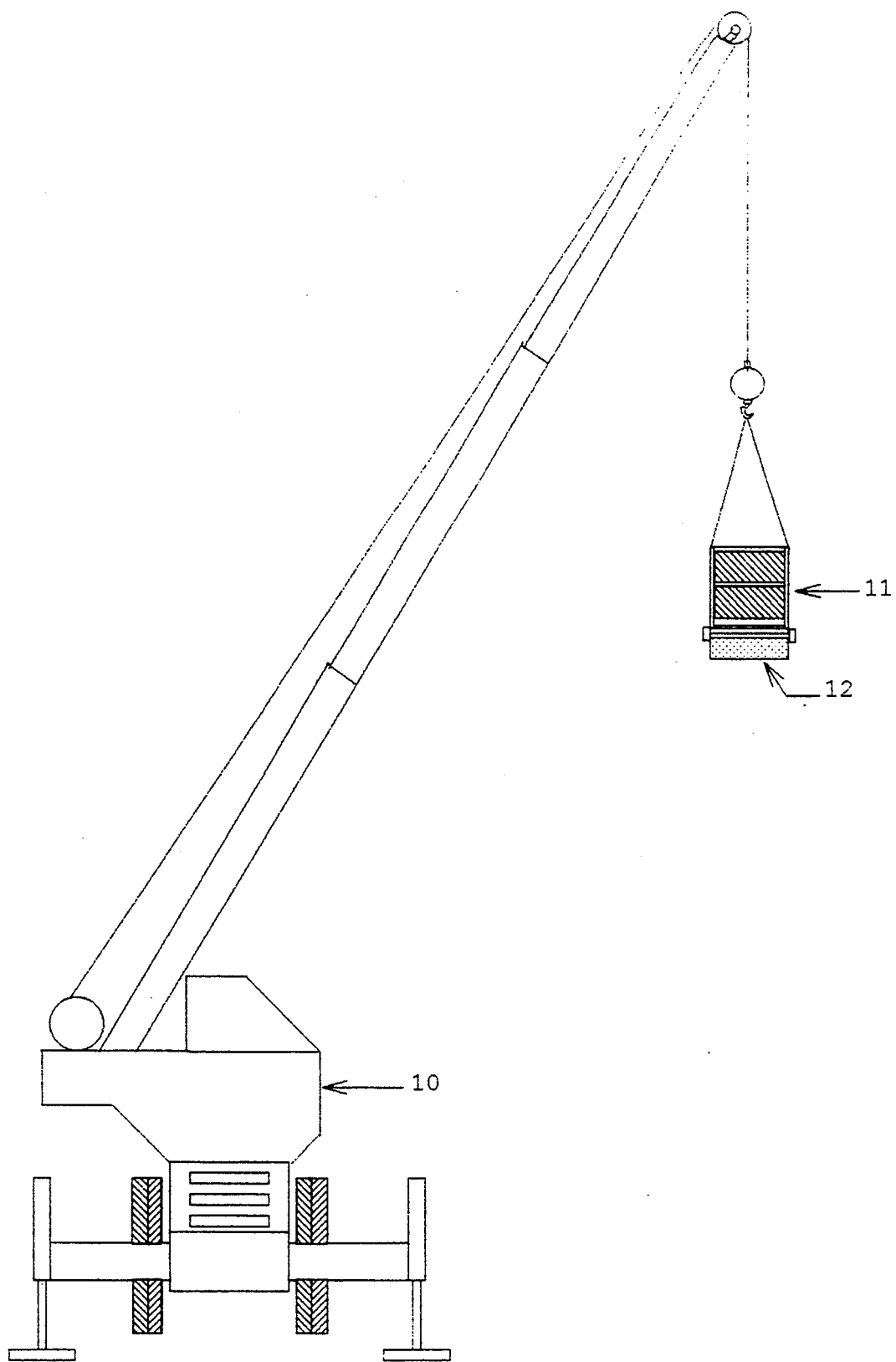
FIG. 1 is a somewhat schematic view of a crane supporting a personnel platform and a test-weight.

Referring more specifically to the drawings, FIG. 1 illustrates a crane 10 supporting a personnel platform 11 and an attached test-weight 12 while carrying out a trial lift and proof test (load test) mandated by OSHA. The mandated trial lift and proof test is for the safety of the workmen that will occupy the personnel platform after the test-weight is removed from the personnel platform, if the test result is satisfactory.

OSHA requires the load test to be carried out each time a crane is set up, as previously explained in describing the background of the invention. The need for frequent testing has justified the making of preformed test-weights capable of being quickly and releasably attached to a personnel platform.

Figure 2:
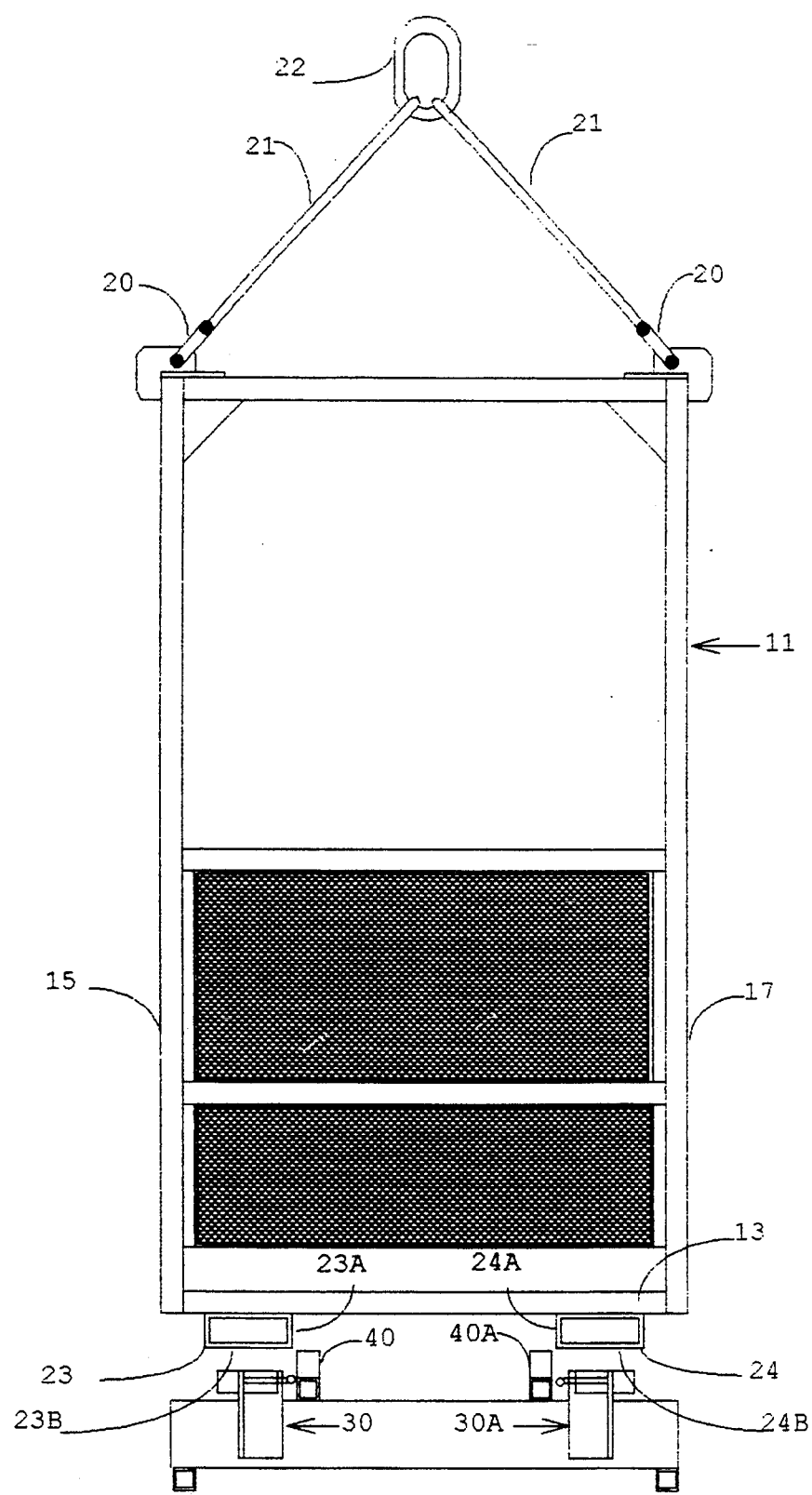
FIG. 2 is an exploded side view of the personnel platform and the test-weight.
Figure 3:
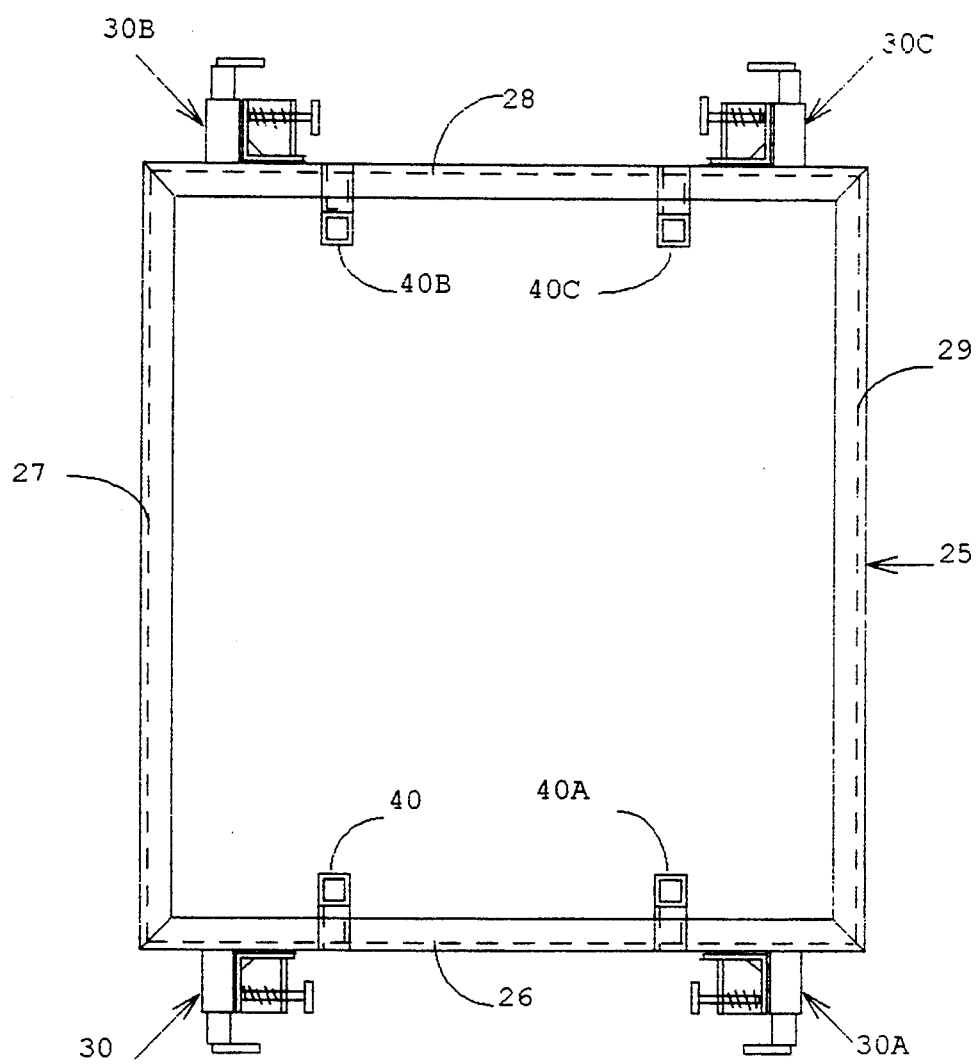
FIG. 3 is a top plan view of the test-weight.

The present embodiment of the personnel platform 11 and its test-weight 12 is illustrated in FIG. 2. The personnel platform 11 has a floor 13 and side walls 14, 15, 16, and 17. A bolt type shackle 20 connects the personnel platform 11 to a four leg bridle 21 depending from a master link 22.

Suitably spaced forklift tubes 23 and 24 are welded to the lower frame of the floor 13 of the personnel platform. The forklift tubes 23, 24 enable the arms of a fork-lift truck to pick up the personnel platform and readily move it from place to place as desired. The provision of forklift tubes on a personnel platform for use in combination with latching assemblies to attach test weights to the personnel platform has not heretofore been known, to applicant's knowledge.

In the illustrated embodiment, the test-weight 12 is a pan filled with sufficient concrete to provide the specified amount of weight for the test-weight 12. The concrete is held in place by an annular steel frame 25. Legs 26, 27, 28, and 29 of the steel frame 25 extend in parallel relation with the personnel platform's side walls 14, 15, 16, and 17, respectively, when the personnel platform and test-weight are assembled as in FIG. 4.

Latching assemblies, broadly indicated at 30, 30A, 30B and 30C are located near the corners of the test-weight 12. The structure and function of the four latching assemblies are the same and an explanation of the latching assembly 30 will suffice for an understanding of the structure and function of all four of the latching assemblies.

Figure 5:
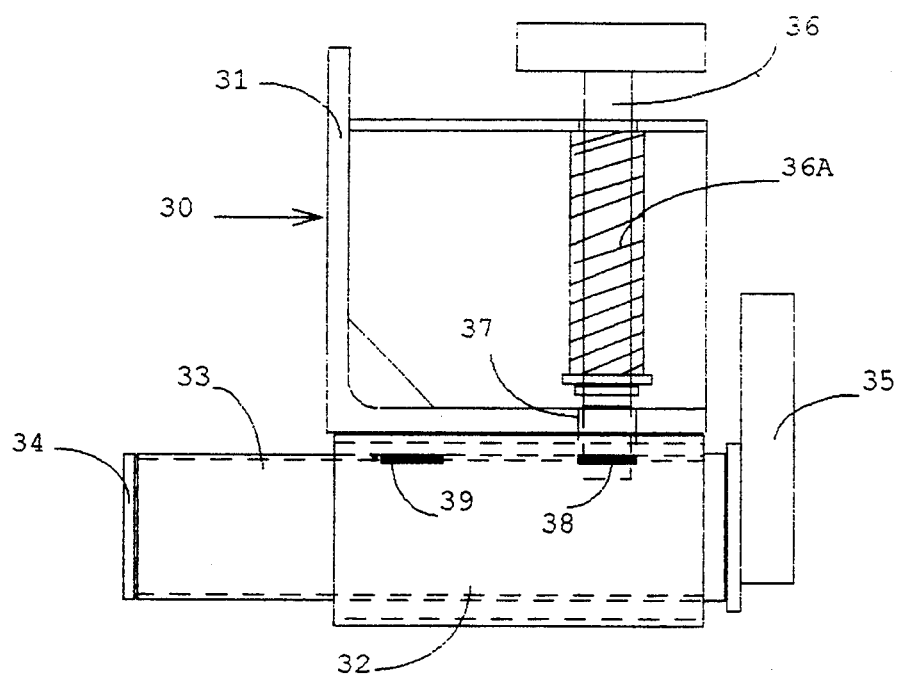
FIG. 5 is a top view of one of the latching assemblies removed from the frame of the test-weight and showing the lock-bolt in its extended or latching position.
Figure 6:
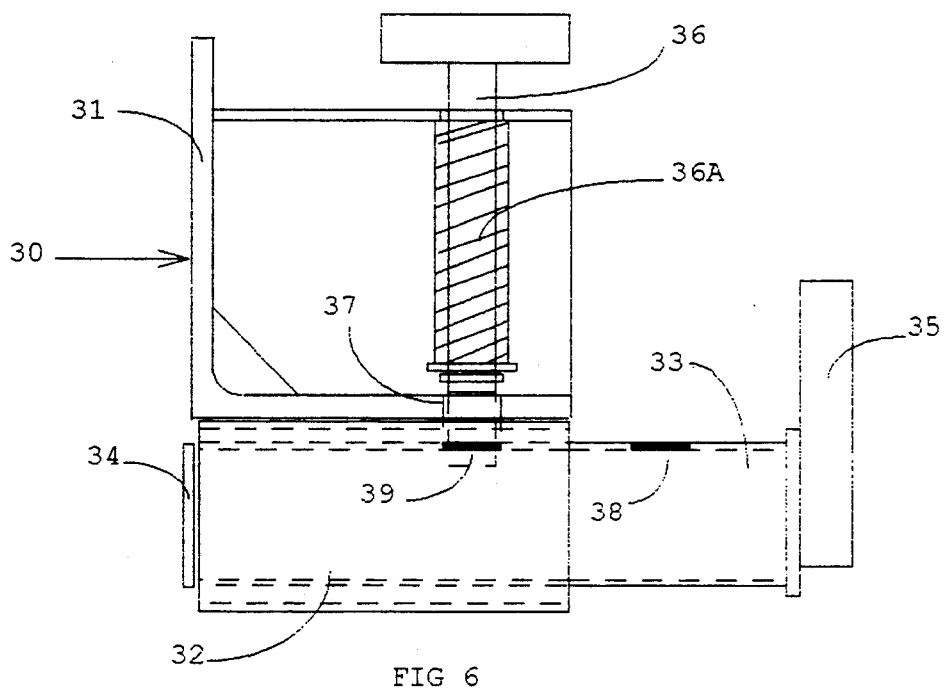
FIG. 6 is a view similar to FIG. 5 but showing the lock-bolt in its retracted or inactive position.

Referring to FIGS. 5 and 6, the latching assembly 30 includes an L-shaped bracket 31, one leg of which is welded to the frame 25. The other leg of the bracket 31 supports an open ended tubular housing or cylinder 32. A heavy steel lock-bolt 33 is slidably mounted in the cylinder 32 and extends through the ends of the cylinder. The lock-bolt 33 is prevented from sliding out of the cylinder 32 by a lip 34 engageable with the inner end of the cylinder 32 and a handle 35 engageable with the outer end of the cylinder.

A spring-pressed plunger 36 is mounted on the bracket 31 in perpendicular relation to the cylinder 32 and lock-bolt 33. The leg of the bracket 31 that supports the cylinder 32 has an opening 37 through it in registry with the plunger 36. The plunger 36 is normally urged by the spring 36A through the opening 37 and into engagement with the lock-bolt 33. The lock-bolt has a hole 38 that registers with the plunger 36 when the lock-bolt is moved to the active position of FIG. 5, and a hole 39 that registers with the plunger 36 when the lock-bolt is moved to the inactive position of FIG. 6. When the plunger 36 enters one of the holes 38, 39, the lock-bolt 33 is held in either its active position of FIG. 5 or the inactive position of FIG. 6.

Alignment guides 40, 40A, extend upwardly from the leg 26 of the test-weight's annular frame 25 in inwardly spaced relation to the latching assemblies 30, 30A. Corresponding alignment guides 40B, 40C extend upwardly from the leg 28 of the test-weight's annular frame 25 in inwardly spaced relation to the latching assemblies 30B, 30C. The alignment guides 40, 40A and 40B, 40C are fixed to the test-weight 12 in position to be closely adjacent the inner walls 23A and 24A of the forklift tubes 23, 24 after the personnel platform 11 has been lowered for attachment to the test-weight 12, as in FIG. 4. So positioned, the alignment guides 40, 40A, 40B and 40C effectively align the latching assemblies 30, 30A, 30B and 30C with the open ends of the forklift tubes 23 and 24.

Figure 4:
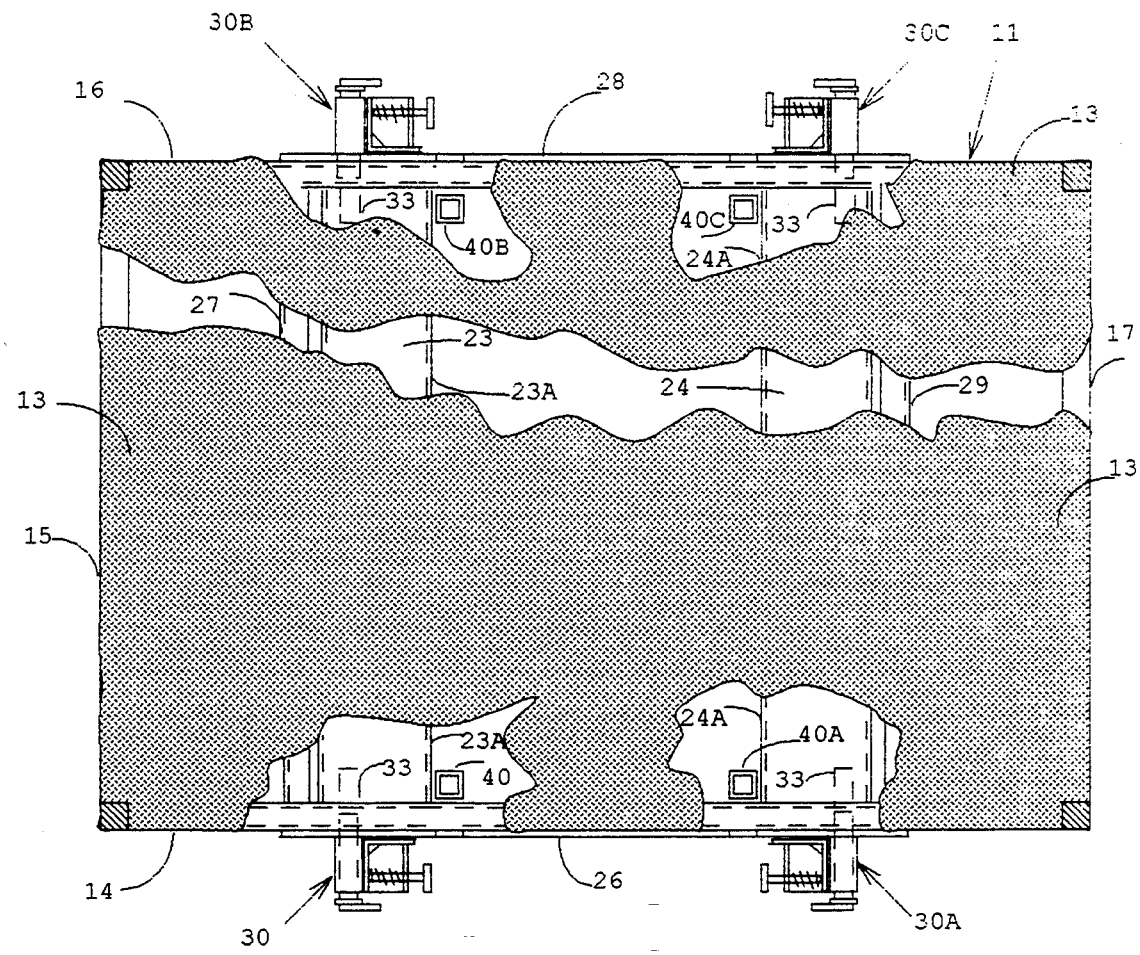
FIG. 4 is an enlarged plan view, partially in section and with parts broken away, showing the lock-bolts engaged with the forklift tubes for attachment of the test-weight to the personnel platform.

FIG. 4 shows the personnel platform 11 operatively engaged with the test-weight 12 for a load test. As the personnel platform 11 was lowered by a crane onto the test-weight 12, the upstanding alignment guides 40, 40A, 40B and 40C on the test-weight were used to engage the inner walls 23A and 24A of the forklift tubes 23, 24 and guide the forklift tubes into position with their open ends in registry with the latching assemblies 30, 30A, 30B and 30C.

When the personnel platform 11 is positioned on the test-weight 12 as shown in FIG. 4, a workman manipulates the spring-pressed plunger 36 on the latching assemblies 30, 30A, 30B and 30C to release the lock-bolts 33 from the inactive position of FIG. 6. The lockbolts are then manually moved to the active position of FIG. 5 with the lock-bolts extending into the open ends of the forklift tubes 23 and 24.

When the personnel platform is lifted for a load test, the lower walls 23B and 24B of the forklift tubes 23 and 24 move against the lock-bolts 33 to thereby quickly, effectively, and releasably attach the test-weight 12 to the personnel platform 11 for a load test.

When the personnel platform 11 and the attached test-weight 12 are returned to the ground after the load test is completed, a workman quickly and easily removes the test-weight from the personnel platform by simply manipulating the spring-pressed plungers to unlock the lock-bolts and then manually retract the lock-bolts from the forklift tubes into the inactive position of FIG. 6.

The latching assemblies remain intact on the test-weight 12, ready to be activated to connect the test-weight 12 to the personnel platform 11 for the next load test.

There is thus provided a novel personnel platform with forklift tubes which cooperate with latching assemblies integrated with the test-weight to enable quick and reliable engagement and disengagement of the test-weight and personnel platform without the risk of losing parts.

Although specific terms have been used in describing the invention, they have been used in a descriptive and generic sense only and not for the purpose of limitation, the scope of the invention to be determined by a consideration of the appended claims with the specification and the applicable prior art.

I claim:

1. Load testing apparatus for releasably attaching a test-weight to and releasing a test-weight from, a personnel platform having a floor, open ended forklift tubes extending between two sides of the personnel platform beneath the floor of the platform and means for suspending the personnel platform from a crane, said load testing apparatus comprising:

a test-weight including means integrated with the test-weight for releasably attaching the test-weight to and releasing the test-weight from the forklift tubes on the personnel platform, whereby the forklift tubes on the personnel platform may be guided into registry with the means integrated with the test-weight for releasably attaching the test-weight to and releasing the test-weight from the forklift tubes on the personnel platform while a crane positions the personnel platform on the testweight.

2. The invention of claim 1 wherein said means comprises latching assemblies fixed to two opposed sides of the testweight in position to register with the open ends of the forklift tubes when the personnel platform and the test-weight are operatively oriented for attaching the test-weight to the personnel platform, and upstanding alignment guides on the test-weight that are engageable with the forklift tubes on the personnel platform to guide the forklift tubes into registry with the latching assemblies as the crane lowers the personnel platform on the test-weight.

3. The invention of claim 2 wherein each latching assembly additionally includes means for locking the lock-bolt in position to engage one end portion of a fork lift tube when the personnel platform is suspended.

4. A method of releasably attaching a test-weight to and removing a test-weight from a personnel platform having means for being suspended, a floor and forklift tubes beneath the floor extending between opposed sides of the personnel platform, said method comprising the steps of:

(a) providing releasable latching assemblies on the test-weight;

(b) providing upstanding guides on the test-weight;

(c) lowering the personnel platform onto the test-weight while using the upstanding guides to register the forklift tubes on the personnel platform with the latching assemblies on the test-load; and (d) releasably attaching the test-load to the forklift tubes.

5. The method of claim 4 which includes the step of locking the lock-bolts in position within the forklift tubes.

6. The invention of claim 2 wherein the latching assemblies include lockbolts releasably engageable with the open end portions of the forklift tubes to attach the test-weight to the personnel platform when the personnel platform is suspended.

* * * * *